United States Patent
Rich

(10) Patent No.: US 11,419,850 B2
(45) Date of Patent: *Aug. 23, 2022

(54) COMBINED ACETYLCHOLINESTERASE INHIBITOR AND QUATERNARY AMMONIUM ANTIMUSCARINIC THERAPY TO ALTER PROGRESSION OF COGNITIVE DISEASES

(71) Applicant: Qaam Pharmaceuticals, LLC, Canandaigua, NY (US)

(72) Inventor: Steven A. Rich, Canandaigua, NY (US)

(73) Assignee: QAAM PHARMACEUTICALS, LLC, Canandaiqua, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/454,862

(22) Filed: Jun. 27, 2019

(65) Prior Publication Data

US 2019/0314332 A1 Oct. 17, 2019

Related U.S. Application Data

(60) Continuation of application No. 15/233,188, filed on Aug. 10, 2016, now Pat. No. 10,376,496, which is a continuation of application No. 14/513,631, filed on Oct. 14, 2014, now Pat. No. 9,980,941, which is a continuation of application No. 13/778,556, filed on Feb. 27, 2013, now Pat. No. 9,034,890, and a division of application No. 13/778,530, filed on Feb. 27, 2013, now Pat. No. 8,969,402, which is a continuation-in-part of application No. 13/325,371, filed on Dec. 14, 2011, now Pat. No. 9,084,753, which is a division of application No. 11/935,483, filed on Nov. 6, 2007, now Pat. No. 8,097,633.

(60) Provisional application No. 60/865,893, filed on Nov. 15, 2006.

(51) Int. Cl.
| | |
|---|---|
| *A61K 31/40* | (2006.01) |
| *A61K 31/325* | (2006.01) |
| *A61K 31/27* | (2006.01) |
| *A61P 25/28* | (2006.01) |
| *A61K 31/137* | (2006.01) |
| *A61K 31/216* | (2006.01) |
| *C07D 207/12* | (2006.01) |
| *C07D 451/00* | (2006.01) |
| *A61K 31/445* | (2006.01) |
| *A61K 31/435* | (2006.01) |
| *A61K 31/4015* | (2006.01) |
| *A61K 31/438* | (2006.01) |
| *A61K 31/165* | (2006.01) |
| *A61K 31/407* | (2006.01) |
| *A61K 31/20* | (2006.01) |
| *A61K 31/201* | (2006.01) |
| *A61K 31/202* | (2006.01) |
| *A61K 9/00* | (2006.01) |
| *A61K 9/70* | (2006.01) |
| *A61K 31/439* | (2006.01) |

(52) U.S. Cl.
CPC ............ *A61K 31/40* (2013.01); *A61K 9/0014* (2013.01); *A61K 9/0053* (2013.01); *A61K 9/7023* (2013.01); *A61K 31/137* (2013.01); *A61K 31/165* (2013.01); *A61K 31/20* (2013.01); *A61K 31/201* (2013.01); *A61K 31/202* (2013.01); *A61K 31/216* (2013.01); *A61K 31/27* (2013.01); *A61K 31/407* (2013.01); *A61K 31/4015* (2013.01); *A61K 31/435* (2013.01); *A61K 31/438* (2013.01); *A61K 31/439* (2013.01); *A61K 31/445* (2013.01); *C07D 207/12* (2013.01); *C07D 451/00* (2013.01)

(58) Field of Classification Search
CPC ...... A61K 31/27; A61K 31/40; A61K 31/325; A61P 25/28
See application file for complete search history.

(56) References Cited

U.S. PATENT DOCUMENTS

| | | |
|---|---|---|
| 5,346,906 A | 9/1994 | Baker et al. |
| 5,861,431 A | 1/1999 | Hildebrand et al. |
| 6,063,808 A | 5/2000 | Fabiano et al. |
| 6,204,285 B1 | 3/2001 | Fabiano et al. |
| 6,255,502 B1 | 7/2001 | Penkler et al. |
| 7,091,236 B1 | 8/2006 | Roberts et al. |
| 8,343,467 B2 | 1/2013 | Woehrmann et al. |
| 8,404,701 B2 | 3/2013 | Chase et al. |
| 8,877,768 B2 | 11/2014 | Chase et al. |
| 9,561,218 B2 * | 2/2017 | Clarence-Smith ... A61K 31/445 |
| 2003/0225031 A1 | 12/2003 | Quay |

(Continued)

FOREIGN PATENT DOCUMENTS

WO 2009052353 A2 4/2009

OTHER PUBLICATIONS

Robert, P.H. L'Encephale, Nov. 1999, Spec. No. 5, Abstract.*

(Continued)

*Primary Examiner* — Samira J Jean-Louis
(74) *Attorney, Agent, or Firm* — Brown & Michaels, PC

(57) ABSTRACT

A method administers quaternary ammonium anti-cholinergic muscarinic receptor antagonists in combination with acetyl-cholinesterase inhibitors to treat either cognitive impairment or acute delirium. This therapy results in a modification of a cognitive disorder or disease, namely a slow down in the disease progression. In one preferred embodiment, the disease is dementia with Lewy Bodies. New formulations for quaternary ammonium anti-cholinergic muscarinic receptor antagonists are also disclosed.

39 Claims, 3 Drawing Sheets

(56) References Cited

U.S. PATENT DOCUMENTS

| | | |
|---|---|---|
| 2004/0082644 A1 | 4/2004 | Korsten |
| 2006/0018839 A1 | 1/2006 | Ieni et al. |
| 2006/0142241 A1 | 6/2006 | Yoo |
| 2011/0086950 A1 | 4/2011 | Changping |
| 2011/0201597 A1 | 8/2011 | Chase et al. |
| 2014/0350281 A1 | 11/2014 | DeMattei et al. |
| 2015/0086640 A1 | 3/2015 | Staniforth et al. |

OTHER PUBLICATIONS

Mashour et al. Science Translational Medicine, 2011, vol. 3, Iss. 114, Abstract.*
Ancelin et al., "Non-degenerative mild cognitive impairment in elderly people and use of anticholinergic drugs longitudinal cohort study", BMJ, doi:10.1136/bmj.38740.439664.DE, 5 pages, 2006.
Aschenbrenner et al., Drug Therapy in Nursing, p. 324,2009.
Campbell et al., "Use of anticholinergics and the risk of cognitive impairment in an African American population", Neurology, vol. 75, pp. 152-159, 2010.
Carnahan et al., "The Concurrent Use of Anticholinergics and Cholinesterase Inhibitors: Rare Event or Common Practice?", JAGS vol. 52, pp. 2082-2087, 2004.
Chew et al., "Serum Anticholinergic Activity and Cognition in Patients with Moderate-to-Severe Dementia", Am. J. Geriatr. Psychiatry, vol. 13, pp. 535-538, 2005.
Cooke et al., "Glycopyrrolate in Bladder Dysfunction", South African Medical Journal, vol. 63, p. 3, 1983.
CUVPOSA (glycopyrrolate) oral solution, Product Information Sheet, pp. 6-15, 2010.
DETROL@ LA (tolterodine tartrate) capsules, Product Information Sheet, 12 pages, 2008.
Drinka, "Antimuscarinic Drugs for Overactive Bladder and Their Potential Effects on Cognitive Function in Older Patients", JAGS, vol. 54, pp. 1004-1005, 2006.
Douaud et al., "Preventing Alzheimer's disease-related gray matter atrophy by B-vitamin treatment", PNAS, vol. 110, pp. 9523-9528, 2013.
ENABLEX® (darifenacin) tablets, Product Information Sheet, 16 pages, 2010.
EXELON® Capsule, Product Information Sheet, Novartis, 4 pages, 2002.
EXELON® Patch (rivastigmine transdermal system), Product Information Sheet, LTS Lohmann Therapie Systems AG, 12 pages, 2000.
Ferguson, "Modulation of lymphatic smooth muscle contraction responses by the endothelium", Journal of Surgical Research, vol. 52, pp. 359-363, 1992.
Gish et al., "Memorandum: Age-dependent manifestations of central anticholinergic effects", Department of Health and Human Services Public Health Service Food and Drug Administration Center for Drug Evaluation and Research, 30 pages, 2007.
Hashimoto et al., "Urinary Incontinence: an Unrecognised Adverse Effect with Donepezil", The Lancet, vol. 356, p. 568, 2000.
Iliff et al., "A Paravascular Pathway Facilitates CSF Flow Through the Brain Parenchyma and the Clearance of Interstitial Solutes, Including Amyloid β". Sci. Transl. Med., vol. 4(147):147ra111, 11 pages, 2012.
Janos et al., "Overactive bladder medicines and cognitive testing", Int. J. Clin. Pract., vol. 62, pp. 1637-1642, 2008.
Jewart et al., "Cognitive, Behavioral and Physiological Changes in Alzheimer Disease Patients as a Function of Incontinence Medications", Am. J. Geriatr. Psychiatry, vol. 13, pp. 324-328, 2005.
Jhee et al., "Centrally Acting Antiemetics Mitigate Nausea and Vomiting in Patients with Alzheimer's Disease Who Receive Rivastigmine", Clinical Neuropharmacology, vol. 25, pp. 122-123, 2002.
Kay et al., "Antimuscarinic Drugs for Overactive Bladder and Their Potential Effects on Cognitive Function in Older Patients", JAGS, vol. 53, pp. 2195-2201, 2005.
Kay et al., "Preserving cognitive function for patients with overactive bladder: evidence for a differential effect with darifenacin", Int. J Clin. Pract., vol. 62, pp. 1792-1800, 2008.
Khullar et al., "Prevalence of Faecal Incontinence among Women with Urinary Incontinence", Br. J. Obstet. Gynaecol., vol. 105, pp. 1211-1213, 1998.
Levin et al., "Direct Measurement of the Anticholinergic Activity of a Series of Pharmacological Compounds of the Canine and Rabbit Urinary Bladder", J. Urology, vol. 128, pp. 396-398, 1982.
Lopez et al., "Predictors of progression in patients with AD and Lewy bodies", Neurology, vol. 54, pp. 1774-1779, 2000.
Medline Plus, "Stress incontinence: MedlinePluss Medical Encyclopedia", available at http://www.nlm.nih.gov/medlineplus/ency/article/000891.htm, 5 pages, 2009.
Oken, "Antihistamines, a Possible Risk Factor for Alzheimer's Disease", Medical Hypotheses, vol. 44, pp. 47-48, 1995.
Olichney et al., "Cognitive Decline is Faster in Lewy Body Variant than in Alzheimer's Disease", Neurology, vol. 51, pp. 351-357, 1998.
Ono Pharmaceutical Co., Ltd., "Launch of Rivistach® Patch, for the Treatment of Dementia of Alzheimer's Type", 2 pages, 2011.
Ray et al. "Central Anticholinergic Hypersensitivity in Aging", Journal of Geriatric Psychiatry and Neurology, vol. 5, pp. 72-77, 1992.
ROBINUL® glycopyrrolate tablets, Product Information Sheet, 4 pages, 2010.
Roe et al., "Use of Anticholinergic Medications by Older Adults with Dementia", JAGS, vol. 50, pp. 836-842, 2002.
Rudolph et al., "The Anticholinergic Risk Scale and Anticholinergic Adverse Effects in Older Persons", Arch. Intern. Med., vol. 168, pp. 508-513, 2008.
SANCTURA® (trospium chloride), Product Information Sheet, 12 pages, 2011.
Sink et al., "Dual Use of Bladder Anticholinergics and Cholinesterase Inhibitors: Long-Term Functional and Cognitive Dutcomes", JAGS, vol. 56, pp. 847-853, 2008.
Terry et al., "The Cholinergic Hypothesis of Age and Alzheimer's Disease-Related Cognitive Deficits: Recent Challenges and Their Implications for Novel Drug Development", JPEI, vol. 306, pp. 821-827, 2003.
Tsao et al., "Transient Memory Impairment and Hallucinations Associated with Tolterodine Use", New England Journal of Medicine, vol. 349, pp. 2274-2275, 2003.
Van Eijk et al., "Effect of rivastigmine as an adjunct to usual care with haloperidol on duration of delirium and mortality in critically ill patients: a multicentre, double-blind, placebo-controlled randomised trial", Lancet, vol. 376, pp. 1829-1837, 2010.
VESICARE® (solifenacin succinate) tablets, Product Information Sheet, 16 pages, 2010.
Williams et al., "Survival and mortality differences between dementia with Lewy bodies vs Alzheimer disease", Neurology, vol. 67, pp. 1935-1941, 2006.
Verdejo et al. Anales de Medicina, 1992, vol. 9, No. 3, abstract only (cited by Examiner on Dec. 10, 2014 in U.S. Appl. No. 13/325,371).
International Search Report and Written Opinion dated Sep. 2, 2016, International Application No. PCT/US2016/035916.
Collomb et al., "Composition of fatty acids in cow's milkfat produced in the lowlands, mountains and highlands of Switzerland using high-resolution gas chromatography," International Dairy Journal 12 (2002) 649-659.
Pubchem Open Chemistry Database, 2005, Compound Summary for CID 11693, Glycopyrrolate, retrieved from https://pubchem.ncbi.nlm.nih.gov/compound/glycopyrrolate.
Simard et al., "Locating high-affinity fatty acid-binding sites on albumin by x-ray crystallography and NMR spectroscopy," PNAS, 2005, 102(50), 17958-17963.
Alcalde et al. "A Simple Halide-to-Anion Exchange Method for Heteroaromatic Salts and Ionic Liquids", Laboratory of Organic Chemistry, Faculty of Pharmacy, University of Barcelona; Apr. 2012.
McKeith et al. "Efficacy of rivastigmine in dementia with Lewy bodies: a randomised, double-blind, placebo-controlled International study"; The Lancet, vol. 356, Dec. 2000.

(56) References Cited

OTHER PUBLICATIONS

Sarter et al. "Developmental origins of the age-related decline in cortical cholinergic function and associated cognitive abilities"; Neurbiology of Aging 25; 2004.

Nelson et al. "Acetylcholinesterase Inhibitor Treatment is Associated with Relatively Slow Cognitive Decline in Patients with Alzheimer's Disease and AD + DLB", J Alzheimers Dis. Jan. 2009; 16(1): 29-34.

Cummings, J. "Cholinesterase inhibitors for treatment of dementia associated with Parkinson's disease", J Neurol Neurosurg Psychiatry Jul. 2005;76(7):903-4.

Aarsland et al. "Role of cholinesterase inhibitors in Parkinson's disease anddementia with Lewy bodies."; J Geriatr Psychiatry Neurol. Sep. 2004;17(3):164-71.

Pagano et al. "Cholinesterase inhibitors for Parkinson's disease: a systematic review and meta-analysis."; J Neurol Neurosurg Psychiatry. Jul. 2015;86(7):767-73.

Guay, David, Trospium chloride; an update on a quaternary anticholinergic for treatment of urge urinary Incontinence, Ther Clin Risk Manag., Jun. 2005; 1(2): 157-167, Minneapolis, MN, USA.

Langguth P, Kubis A, Krumbiegel G, et al. "Intestinal absorption of the quaternary trospium chloride permeability-lowering factors and bioavailabilities for oral dosage forms". Eur J Pharm Biopharm. 1997;43:265-72, Elsevier Science.

* cited by examiner

COMBINED ACETYLCHOLINESTERASE INHIBITOR AND QUATERNARY AMMONIUM ANTIMUSCARINIC THERAPY TO ALTER PROGRESSION OF COGNITIVE DISEASES

REFERENCE TO RELATED APPLICATIONS

This application is a continuation of co-pending application Ser. No. 15/233,188, filed Aug. 10, 2016, entitled "COMBINED ACETYLCHOLINESTERASE INHIBITOR AND QUATERNARY AMMONIUM ANTIMUSCARINIC THERAPY TO ALTER PROGRESSION OF COGNITIVE DISEASES", which is a continuation application of application Ser. No. 14/513,631, filed Oct. 14, 2014, entitled "COMBINED ACETYLCHOLINESTERASE INHIBITOR AND QUATERNARY AMMONIUM ANTIMUSCARINIC THERAPY TO ALTER PROGRESSION OF COGNITIVE DISEASES", now U.S. Pat. No. 9,980,941, issued May 29, 2018, which is a divisional of application Ser. No. 13/778,530, filed Feb. 27, 2013, entitled "COMBINED ACETYLCHOLINESTERASE INHIBITOR AND QUATERNARY AMMONIUM ANTIMUSCARINIC THERAPY TO ALTER PROGRESSION OF COGNITIVE DISEASES", now U.S. Pat. No. 8,969,402, issued Mar. 3, 2015, which is a continuation-in-part application of application Ser. No. 13/325,371, filed Dec. 14, 2011, entitled "NEW USES FOR QUATERNARY AMMONIUM ANTICHOLINERGIC MUSCARINIC RECEPTOR ANTAGONISTS IN PATIENTS BEING TREATED FOR COGNITIVE IMPAIRMENT OR ACUTE DELIRIUM", now U.S. Pat. No. 9,084,753, issued Jul. 21, 2015, which is a divisional patent application of application Ser. No. 11/935,483, filed Nov. 6, 2007, entitled "NEW USES FOR QUATERNARY AMMONIUM ANTICHOLINERGIC MUSCARINIC RECEPTOR ANTAGONISTS IN PATIENTS BEING TREATED FOR COGNITIVE IMPAIRMENT OR ACUTE DELIRIUM", now U.S. Pat. No. 8,097,633, issued Jan. 17, 2012, which claims one or more inventions which were disclosed in Provisional Application No. 60/865,893, filed Nov. 15, 2006, entitled "Use of Glycopyrrolate to Remedy Incontinence in Patients Being Treated For Cognitive Impairment or Acute Dementia". Application Ser. No. 14/513,631 is also a continuation of application Ser. No. 13/778,556, filed Feb. 27, 2013, entitled "COMBINED ACETYLCHOLINESTERASE INHIBITOR AND QUATERNARY AMMONIUM ANTIMUSCARINIC THERAPY TO ALTER PROGRESSION OF COGNITIVE DISEASES". The benefit under 35 USC § 119(e) of the United States provisional application is hereby claimed, and the aforementioned applications are hereby incorporated herein by reference.

FIELD OF THE INVENTION

The invention pertains to the field of treating patients suffering from various cognitive disorders. More particularly, the invention pertains to improvements in cognitive function in patients treated with acetyl-cholinesterase inhibitors in combination with quaternary ammonium anti-cholinergic muscarinic receptor antagonist.

BACKGROUND OF THE INVENTION

Neurodegenerative diseases impart costs on individuals and society in terms of loss of function, costs of care, and the personal loss of identity associated with pain and suffering. Such diseases or cognitive disorders include, but are not limited to Alzheimer's Disease, Dementia with Lewy Body, Parkinson's Disease, and Progressive Supranuclear Palsy.

Cognitive impairment is a serious neurological condition which is very common in the elderly. It is estimated that approximately one-third of people who live to be over 80 years of age will be diagnosed with some form of cognitive impairment, or dementia. Cognitive impairment can result from a variety of disease processes, such as, but not limited to:

Neurodegenerative dementia:
  Alzheimer's Disease
  Pick's Disease
  Progressive Supranuclear Palsy
  Dementia with Lewy Bodies
  Parkinson's Disease
  Fronto-temporal Dementia
Vascular Diseases:
  Stroke
  Multi-infarct dementia
  Subarachnoid hemorrhage
  Head Trauma
Infections:
  Post-encephalitic dementia
  Syphilis
  Herpetic encephalitis
Congenital abnormalities:
  Trisomy 21
Toxic Brain Injuries:
  Wernike Encephalopathy
  Krorsakoff psychosis
  Alcoholic amnesic syndrome
  Alcoholic dementia The primary result of this general condition is a universal decline in the intellectual function of the individual, usually resulting in significant impediments to normal daily functions. While there is currently no disease modifying therapy available for most forms of cognitive impairment, certain treatments are available to treat the symptoms and improve cognitive functioning to varying degrees, which can alleviate or at least delay the need for institutionalizing these individuals.

It has been determined that the decline of the neurotransmitter chemical acetylcholine in the brain is one of the primary mechanisms of declining mental function. Medications that can prevent or at least minimize the breakdown of acetylcholine in the brain provide significant improvement in the cognitive abilities of patients diagnosed with cognitive impairment. These medications are commonly referred to as acetyl-cholinesterase inhibitors. However, as with any medication, there are side effects. For example, acetyl-cholinesterase inhibitors exacerbate urinary and fecal incontinence in patients administered these drugs. Other side effects include a reduced heart rate, sweating, vasodilation and increased bronchial secretions. Such side effects may be so uncomfortable for many elderly patients that the patient is unable to tolerate effective dosing of acetyl-cholinesterase inhibitors to successfully treat the cognitive impairment.

Attempts to ameliorate these undesirable side effects in cognitively impaired patients include the administration of, for example, antimuscarinic anti-cholinergic drugs (commonly called "anti-muscarinics"). These drugs block the peripheral stimulation of the acetylcholine receptors. Unfortunately, however, the use of these medications to treat the side effects of acetyl-cholinesterase inhibitors mentioned previously often contribute to cognitive impairment, which is what is being treated by the acetyl-cholinesterase inhibitor in the first place. Thus, benefits of using these drugs must be balanced with the risks of exacerbating the existing cognitive impairment. As a result, many patients are either inadequately treated or go untreated.

Over the years, researchers have studied the cognitive effects of anti-cholinergic drugs and have found that anti-cholinergic muscarinic drugs cause cognitive decline in the elderly and further cognitive decline in those already impaired. In fact, many practitioners refer to the dilemma regarding treatment of impairments in cognitive function in combination with incontinence as choosing between "your brain versus your bladder". When prescribing medications, a practitioner has to work with their patients and their families and often decide whether to treat the incontinence caused by the medications being used to try to improve cognitive function, which would result in further detriment of cognitive function, or instead rely on alternative solutions to incontinence issues (including the often embarrassing use of adult diapers, or even institutionalization of the incontinent patient).

In addition to cognitive impairment, a more severe problem often afflicts the elderly and is referred to as acute delirium. The primary indicators are a pronounced change in mental status that rapidly fluctuates, the inability to maintain normal degrees of attention, disorganized thinking and vacillating levels of consciousness. Acute delirium can often result from a severe medical illness, recent surgery and use of several medications or interactions between various medications. The impact of acute delirium on patients is severe and often chronic, frequently leading to death.

While the neurological mechanism by which acute delirium occurs is not completely understood, like cognitive impairment, the neurotransmitter acetylcholine is thought to play a significant role. In patients suffering from dementia, a decline in acetylcholine has been seen in post mortem studies. As with treatments for cognitive impairment, the use of acetyl-cholinesterase inhibiting medications has been determined to prevent, to varying degrees, the breakdown of acetylcholine in the brain. However, the undesired side effects outside the central nervous system (CNS) that have been discussed above often result. In order to minimize these problems, the administration of drugs that block the peripheral effects of acetyl-cholinesterase inhibitors act would be desirable. Unfortunately, in a manner similar to other cognitive impairments, anti-cholinergics frequently contribute to the underlying problem by causing central nervous system toxicity.

There is thus a severe need to treat patients suffering from various forms of cognitive impairment as well as those suffering from acute delirium with an effective amount of medication to minimize or entirely alleviate these conditions without imposing upon them the undesired peripheral effects discussed previously, especially urinary and/or fecal incontinence, nausea, bradychardia, bronchorrhea and/or bronchospasm which often coexist with these cognitive impairments. The desire is to be able to administer the most efficacious type and amount of medication to treat the neurological condition without increasing the unwanted side effects of high doses of those medications. This balance has yet to be achieved in modern clinical practice.

There is also a need for treatments that alter the disease progression of progressive dementias and other cognitive impairments.

SUMMARY OF THE INVENTION

A method administers quaternary ammonium anti-cholinergic muscarinic receptor antagonists in combination with acetyl-cholinesterase inhibitors to treat cognitive impairment and/or acute delirium. This therapy results in a modification of the disease, namely a slow down in the disease progression. In one preferred embodiment, the disease is dementia with Lewy Bodies. In one preferred embodiment, the quaternary ammonium anti-cholinergic muscarinic receptor antagonist is glycopyrrolate and the acetyl-cholinesterase inhibitor is rivastigmine.

The quaternary ammonium anti-cholinergic muscarinic receptor antagonist prevents or substantially ameliorates the undesired side effects of acetyl-cholinesterase inhibitors, which permits the administration of higher doses of acetyl-cholinesterase inhibitors than patients could otherwise tolerate. The use of the compounds of the invention permits the administration of optimum therapeutic dosages of acetyl-cholinesterase inhibitors, thus maximizing the beneficial effect of the therapeutic drugs. Suitable quaternary ammonium anti-cholinergic muscarinic receptor antagonists include the drugs trospium and glycopyrrolate.

A further embodiment of administering quaternary ammonium anti-cholinergic muscarinic receptor antagonists to patients suffering from cognitive disorders, in general, such as dementia, acute dementia and dementia with Lewy Bodies, who are also being administered the acetyl-cholinesterase inhibitor rivastigmine, results in a marked improvement in cognitive function, in addition to an improvement in controlling the adverse effects of excessive acetylcholine including, but not limited to, urinary and/or fecal incontinence, nausea, bradychardia, bronchorrhea and bronchospasm.

BRIEF DESCRIPTION OF THE DRAWINGS

FIG. 1 shows disease progression in a patient, A L, versus expected disease progression.

DETAILED DESCRIPTION OF THE INVENTION

Figure 1:
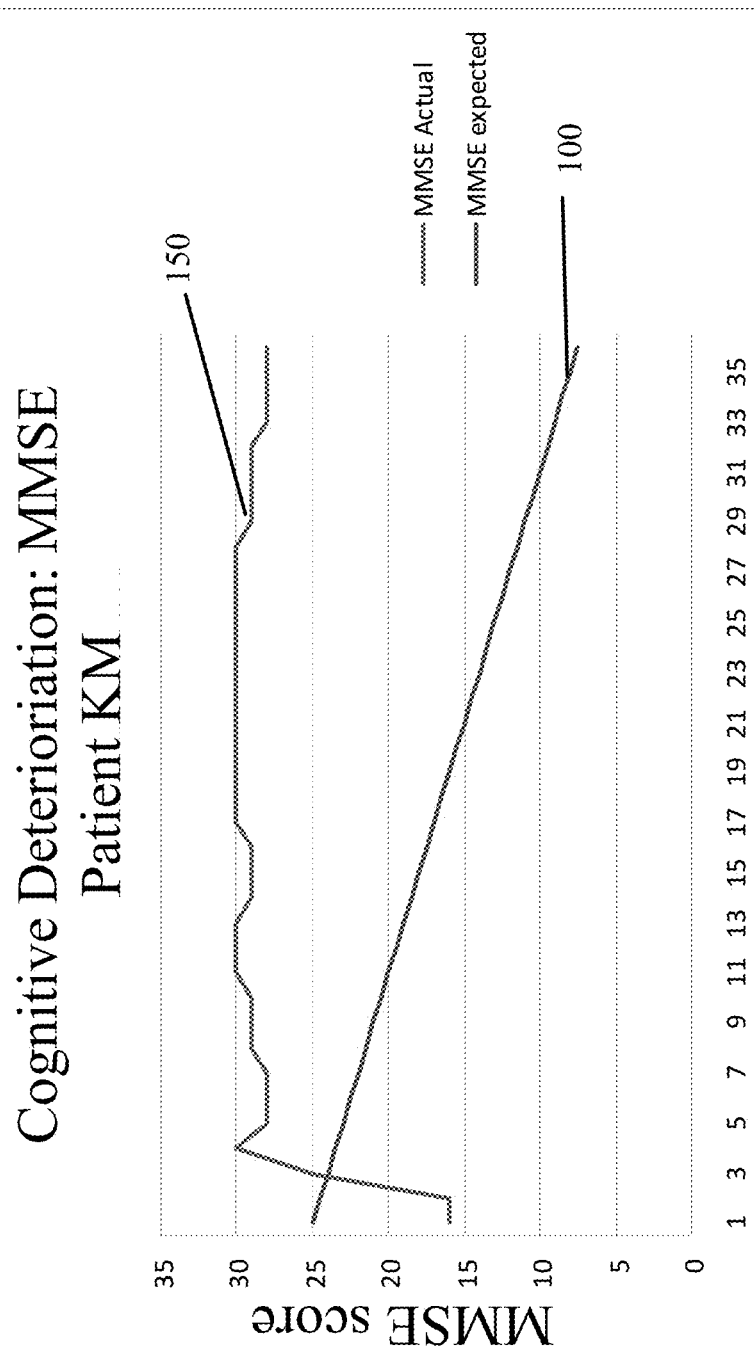
FIG. 1 shows disease progression in a patient, K M, versus expected disease progression.

All known treatments for dementia and other cognitive disorders/impairments treat the symptoms; there are currently no treatments that modify of alter the course of the disease. In other words, there are no treatments that are able to stop or even slow the progression of the disease. In addition, the dosages of the treatments currently available are limited by their side effects.

In methods described herein, combination therapies use acetyl-cholinesterase inhibitors in combination with quaternary ammonium anti-cholinergic muscarinic receptor antagonists to slow the progression of cognitive disease. These therapies result in disease modification of neurodegenerative diseases and certain developmental diseases by pharmacologically enhanced cerebrospinal fluid perfusion. These therapies alter the disease progression by slowing the cognitive deterioration of the patient.

Certain developmental disorders, particularly the Autism Spectrum Disorders, may share a neurodegenerative process, as suggested by the observed fact that normal development is often interfered with at some point after the first year of age. Increasing data suggests that neurodegenerative processes may reflect impaired clearance of endogenous molecules from the central nervous system. Suspected molecules include beta amyloid, alpha synuclein, tau, and numerous modifications of these molecules that occur through endogenous metabolic processes.

Despite the development of technologies for early detection of neurodegenerative processes, such as radio labeled antibodies against amyloid, the clinical role of such interventions has been limited by the fact that there is no disease modifying treatment available, and justification for the cost of these diagnostic interventions is difficult.

At this time, there is no disease modifying therapy available for neurodegenerative, developmental disorders. Anecdotal data has suggested several subjects to seem to have disease remittive effects from pharmacologic intervention, although these do not turn out to be supported in randomized control trials. Randomized controlled trials of numerous classes of agents including, but not limited to, antibodies against beta-amyloid, vaccines against beta amyloid, anti-inflammatory agents, corticosteroids, HMG Co-A reductase inhibitors, angiotension converting enzyme inhibitors, ginkgo biloba, anti-oxidants and monotherapy with highest tolerated doses of acetylcholinesterase inhibitors, have been unsuccessful in altering the deterioration of intellectual function.

Recently described processes for circulation of cerebrospinal fluid (CSF) in the brain may explain the variable experience of patients with slowing, or stabilizing a neurodegenerative process. This includes the "glymphatic" system described as a means for rapid perfusion of the brain interstitial spaces with CSF (Iliff et al., "A Paravascular Pathway Facilitates CSF Flow Through the Brain Parenchyma and the Clearance of Interstitial Solutes, Including Amyloid β". Sci Transl Med, 15 Aug. 2012: Vol. 4, Issue 147, p. 147ra111, herein incorporated by reference), and may have identified the potential clearing mechanism.

The lymphatics system of the human body is under neurological control and numerous pharmacological agents have been described that interact with the lymphatic system, outside of the central nervous system. Many of these pharmacological agents include commonly used medicines in patients with neurodegenerative diseases including adrenergic, serotonergic and acetylcholinergic medications. Acetylcholine is known to induce dilation and enhanced flow of lymphatic pathways in humans.

It is therefore likely that pharmacological agents may influence the rate of clearance of potentially toxic molecules from the central nervous system and that disease processes may represent impairment of these clearing mechanisms.

With a particular focus on the acetylcholine system, cholinergic receptor agonists have been shown to improve lymphatic flow in the peripheral lymphatic system. Despite numerous clinical trials, there is no evidence that monotherapy with acetyl-cholinesterase inhibitors at currently approved maximal doses alters the course of neurodegenerative disorders. However, the degree of inhibition of central nervous system acetyl-cholinesterase achieved with such doses is estimated to be only 30-40%.

As of today, disease modification trials in Alzheimer's disease have been unsuccessful, and have included trials of medications designed to clear amyloid from the central nervous system using immunological technology, as well as attempts to slow the production of amyloid. No clinical studies have focused on enhancement of CSF perfusion as a means for enhanced CNS substrate removal.

Combination Therapies for Reducing Side Effects While Optimizing Efficacy

Not all antimuscarinic drugs are the same. One method of differentiating the various drugs in this category is by lipid solubility. It has been determined that quaternary ammonium compounds of the class of anti-cholinergic muscarinic agents having very low lipid solubility are desired for use within the context of the methods and compounds described herein. As a result of their low lipophilicity (the ability of a compound to dissolve in a lipid medium), these molecules tend not to cross the blood/brain barrier as readily as those having higher lipid solubility. By not crossing this barrier, these compounds do not interfere with the normal function of acetylcholine in the central nervous system, nor do they interfere with the beneficial effects of acetyl-cholinergic inhibitors for the treatment of cognitive impairment or acute delirium. Further, these low lipid solubility quaternary ammonium anti-cholinergic muscarinic receptor antagonist drugs ameliorate the undesired peripheral effects from the use of acetyl-cholinesterase inhibitors, such as urinary and/or fecal incontinence, nausea, bradychardia, bronchorrhea and bronchospasm.

A benefit of using the anti-cholinergic muscarinic agents of the methods and compositions described herein is that the maximum dosing of the acetyl-cholinesterase inhibitor to effectively treat the cognitively impaired patient can be administered and maintained. Higher doses of acetyl-cholinesterase inhibitors may slow, or stop, the degenerative process through mechanisms that include improved clearance of toxic molecules.

The quaternary ammonium anti-cholinergic muscarinic agents for use in the methods described herein are preferably trospium and glycopyrrolate (non-quaternary anti-cholinergic agents include, but are not limited to, oxybutinin, tolterodine, darifenacin and solefenacin). Log P, a recognized parameter proportional to octanol/water partitioning coefficient, is a standard for measuring comparative solubility of a compound in a lipid compared to water. This is the most important physical property that determines whether or not a drug molecule crosses the blood/brain barrier to interfere with the normal functioning of acetylcholine in the central nervous system. A low log P value represents low lipid solubility and low probability of crossing the blood/brain barrier. Both glycopyrrolate and trospium have a low log P based upon their chemical structure. In contrast, the standard anti-muscarinic drugs in use have a log P value as high as 6.076 (tolterodine). Trospium has a log P value of −1.2 at 7.4 pH and the calculated lipophilicity of glycopyrrolate is −75.75, thus making them preferred compounds to achieve the therapeutic goals stated previously within the context of the embodiments described herein.

The quaternary ammonium anticholinergic muscarinic agents may be administered concurrently with any of the various acetyl-cholinesterase inhibitors used to treat cognitive disorders or acute delirium. Such drugs include, but are not limited to:
 donepezil
 rivastigmine
 galantamine
 tacrine
 physostigmine
 pyridostigmine
 neostigmine
 ipidacrine
 phenserine
 icopezil
 zanapezil
 Ambenonium
 Edrophonium
 Huperzine A
 Ladostigil In order to treat patients suffering from cognitive impairment or acute delirium and exhibiting the unwanted adverse effects of excessive acetylcholine including, but not limited to, urinary and/or fecal incontinence, nausea, bradycardia, bronchorrea, brochospasm, and orthostatic hypotension, it is best to combine quaternary ammonium anti-muscarinic agents with suitable acetyl-cholinesterase inhibitors. It is most desirable to administer both classes of drugs intravenously or intramuscularly ("parenterally") or transdermally in patients with acute delirium because these patients are often confused and belligerent and refuse to take oral medications. However, in some cases, oral administration may be successfully achieved.

There is currently no FDA approved drug treatment for acute delirium. Conventional therapy is with dopamine receptor antagonists, otherwise known as antipsychotic medications. Often a patient cannot take such a medication due to a co-existing disease such as Parkinson's Disease, or due to adverse effects. Studies of routine administration of acetyl-cholinesterase inhibitors in addition to haloperidol (an antipsychotic) in intensive care unit patients showed increased mortality (Maarten M J van Eijk et al, The Lancet, Volume 376, Issue 9755, Pages 1829-1837, 27 Nov. 2010, incorporated herein by reference), which is likely related to the untoward effects of these agents in the absence of the peripheral cholinergic blockade provided by quaternary ammonium anti-muscarinic drugs.

For those patients presently exhibiting symptoms of acute delirium, in whom acetyl-cholinesterase inhibitor therapy is being administered, the doses are commonly: donepezil: 5-23 mg/day, galantamine: 4-24 mg/day, rivastigmine: 1.5 to 12 mg/day, physostigmine: 0.5 to 2 mg/day intravenous bolus or up to 10 mcg/minute intravenous infusion. Neostigmine and pyridostigmine have also been used, but dosing is not well defined. In order to prevent the adverse effects of excessive acetylcholine, including but not limited to, urinary and/or fecal incontinence, nausea, bradychardia, bronchorrhea and bronchospasm, glycopyrrolate can be administered at the rate of 0.1 to 0.8 mg/day parenterally or, orally, at the rate of 1 to 8 mg/day. Trospium can be administered at a rate of 20 mg twice a day, or 60 mg once daily.

For those patients being administered maintenance therapy for delirium, glycopyrrolate is administered concurrently with a conventional acetyl-cholinesterase inhibitor, such as donepezil hydrochloride. The dosing for glycopyrrolate is about 0.5 to 4 mg twice a day, with a dosage of about 1-2 mg twice a day most preferred. The donepezil hydrochloride is administered at a rate of about 5 to 20 mg once a day, with a dosage range of about 5 to 10 mg once a day most preferred. Rivastigmine is dosed at 1.5 to 6 mg twice each day and galantamine at 4 to 12 mg twice a day.

The results of various trials using quaternary ammonium anti-cholinergic muscarinic agents in conjunction with acetyl-cholinesterase inhibitors are shown below in the following examples.

Example 1

Incontinence Improvement

The patients only identified by numbers below were administered a therapeutically efficacious amount of glycopyrrolate (0.5 mg to 2 mg twice daily) and monitored for the amount of time indicated.

| Patient | Time of treatment (months) |
|---------|---------------------------|
| '864    | 10                        |
| '105    | 7                         |
| '814    | 7                         |
| '124    | 8                         |
| '291    | 8                         |
| '547    | 8                         |
| '795    | 4                         |
| '104    | 6                         |
| '223    | 4                         |
| '970    | 4                         |
| '568    | 8                         |
| '255    | 6                         |
| '238    | 5                         |

Concurrent with the administration of glycopyrrolate, each of these patients was able to be treated with the maximum effective dosage (10 mg/day) of the acetyl-cholinesterase inhibitor donepezil, which they were unable to tolerate before treatment with glycopyrrolate because of the presence of the undesired side effects noted above. The administration of glycopyrrolate enabled the clinician to administer a dosage of acetyl-cholinesterase inhibitor that provided a measurable cognitive benefit to the patient.

Example 2

Cognitive Function Vs. Incontinence

In this trial, patients were administered either of the non-quaternary ammonium anti-cholinergic muscarinic agents tolterodine (4 mg/day) or oxybutinin (5-20 mg/day), as indicated. The patients were given a Mini-Mental State Examination (MMSE) to determine their cognitive function after being treated with either of these two drugs. The MMSE is a conventionally used test with patients suspected of exhibiting cognitive impairment. The MMSE measures an individual's cognitive ability across several domains of cognitive function. It is an acknowledged standard in the medical field and is appropriate for clinical, office based testing. It is scored from 0 to 30, with score of 30 indicating normal cognitive function.

These patients were then given a therapeutically efficacious amount of glycopyrrolate (2 mg/day) in place of the non-quaternary ammonium anti muscarinic agent and evaluated again using the MMSE test. Their incontinence control was then evaluated and compared against treatment with tolterodine or oxybutinin only.

| Patient | Initial Drug (MMSE) | Glycopyrrolate (MMSE) | Incontinence Control |
|---------|--------------------|-----------------------|---------------------|
| '864    | Tolterodine (14)   | (18)                  | unchanged           |
| '486    | Tolterodine (26)   | (25)                  | improved            |
| '097    | Oxybutinin (28)    | (28)                  | improved            |
| '655    | Oxybutinin (23)    | (22)                  | improved            |

The patients on the initial lipophilic anti-muscarinic agents tolterodine or oxybutinin exhibited stable cognitive function. When the same patients received glycopyrrolate, each patient's cognitive function remained the same, but there was an improvement in three of the four subjects with respect to urinary incontinence control. The reason for this is because they were now able to take adequate doses of medication for incontinence control which did not precipitate or exacerbate the deterioration in cognitive functioning.

A larger study evaluated 39 patients having some form of cognitive impairment with concurrent urinary incontinence. Their MMSE scores ranged from 13 to 29 prior to being given an acetyl-cholinesterase inhibitor. After administering this drug, their individual MMSE scores changed little, as was expected. They were then administered 1 mg twice a day of glycopyrrolate. In 64% of the patients in this group, their incontinence control improved significantly. Interestingly, incontinence control in 33% of this group declined. It is theorized that since these individuals suffered from poor mobility, such as due to hip or leg fractures, they simply could not physically reach a rest room facility in time before becoming incontinent. The incontinence of the remainder of the group remained the same.

Example 3

Rivastigmine with Glycopyrrolate

In this study, six patients with acute delirium were hospitalized and treated at Rochester (N.Y.) General Hospital.

Patient a) Age 83. Diagnosis: Acute delirium, respiratory failure. Condition severe enough to warrant treatment in Intensive Care Unit ("ICU"). Patient was treated with a combination of rivastigmine (1.5 mg titrated to 3 mg, orally, twice each day) and glycopyrrolate (1 mg twice each day, orally). Her cognitive function improved significantly enough that she was to be discharged to a skilled nursing facility upon resolution of her respiratory issues.

Patient b) Age 77. Diagnosis: Acute delirium, urinary incontinence. Upon treatment with 1.5 mg titrated to 3 mg orally, twice a day, with rivastigmine along with 1 mg, twice a day, orally, of glycopyrrolate, the patient's cognitive function improved significantly enough to allow discharge to a skilled nursing facility.

Patient c) Age 86. Diagnosis: Acute delirium, Parkinson's disease. A regimen of 1.5 mg titrated to 6 mg, orally, twice each day, of rivastigmine and 1 mg twice each day, orally, of glycopyrrolate enabled the patient to be discharged to a skilled nursing facility in a relatively short period of time. The internist and the neurologist had no more treatment options for this patient and were looking for a long term placement in a nursing home before the above regime was administered, significantly improving his prognosis.

Patient d) Age 78. Diagnosis: Dementia with Lewy bodies, urinary incontinence. The patient was treated with a regimen of 1.5 mg titrated to 3 mg, orally, twice a day, of rivastigmine and 1 mg twice each day orally of glycopyrrolate. He showed marked improvement in 24 hours and was able to be discharge to his own home after 72 hours. Prolonged hospitalization would have been expected in the absence of the above treatment protocol.

Patient e) Age 80. Diagnosis: Acute delirium, Parkinson's disease. Patient was placed on a regimen of 1.5 mg titrated to 3 mg, orally, twice a day, of rivastigmine and 1 mg, twice each day, orally, of glycopyrrolate. Within days she showed a marked improvement in her choreoathetosis and delirium and was able to be discharged to a skilled nursing facility. She subsequently underwent uncomplicated hip surgery for a fracture, which would not have been possible without this regimen.

Patient f) Age 87. Diagnosis: Acute delirium, Extrapyramidal dysfunction. Patient was treated with 1.5 mg titrated to 3 mg, orally, twice a day of rivastigmine and 1 mg twice each day, orally, of glycopyrrolate. After only 2 days the patient showed significant improvement in cognitive function, cooperation and physical balance. His improvement was so significant that he was discharged to an assisted living level of care instead of the planned discharge to a skilled nursing facility.

Combination Therapy Results in Disease Modification

During the analysis of the results of clinical trials, an interesting and surprising observation was made when the acetyl-cholinesterase inhibitor rivastigmine was coupled with the quaternary ammonium anti-cholinergic muscarinic agent glycopyrrolate. It was noted that patients suffering from various forms of neurodegenerative diseases related to cognitive impairment, such as Alzheimers Disease or Dementia with Lewy bodies, experienced a marked and prolonged improvement in cognitive function. which was uncharacteristic for neurodegenerative processes with this specific combination of drugs. Neurodegenerative diseases routinely progress at disease specific rates and, as mentioned above, no therapy has been shown to modify the rate of cognitive decline. The observation was clinically significant. Disease modification of neurodegenerative processes has huge social, personal and financial implications in an aging population in the developed and developing countries.

Enhancement of CSF perfusion is a means for enhanced CNS substrate removal. The identification of pharmacological means of enhancing CSF turnover in the CNS results in reversing, slowing, or modifying the course of a neurodegenerative disorder, or a developmental disorder on the autism spectrum. Specific targets would include, but not be limited to: beta amyloid, tau, synuclein or any other reputed endogenous molecules that accumulate inappropriately in the central nervous system in the setting of a neurodegenerative disorder or developmental disorder on the autism spectrum. Pharmacological interventions should be assessed on their ability to enhance the turnover of CSF and its transit through the brain and the clearance of suspected molecules and the clinical response to this enhancement.

Acetyl-cholinesterase inhibitors may be used as an example. Current doses of acetyl-cholinesterase inhibitors are reported to reach only 30-40% inhibition of CNS acetylcholine. Higher levels of acetylcholine inhibition are limited by drug-related side effects, which can be modified by the use of quaternary ammonium anti-cholinergic muscarinic receptor antagonists. Preclinical trials could use radiolabeled markers of substances and measure transit time through the central nervous system in the presence or absence of high-level acetyl-cholinesterase inhibition using an acetyl-cholinesterase inhibitor and a quaternary ammonium anti-cholinergic muscarinic receptor antagonist. Monitoring of CSF through spinal fluid drainage procedures could also chemically assess removal of suspect molecules through currently available highly sensitive assays. Studies could be performed in animal models as well as human beings, with currently available technology of radiotracers, PET scans and lumbar punctures with highly sensitive assays.

Clinical trials would involve the patients with mild cognitive impairment, early-stage Alzheimer's disease, signs of an early synuceinopathy (Rapid Eye Movement Sleep Behavioral Disturbance may predict Parkinson's disease, Multisystem Atrophy and Dementia with Lewy Bodies by several decades), and recently identified Autism Spectrum Disorders in children 18 months to 5 years of age. Appropriate markers of disease activity should be measured at baseline and periodically during treatment with high-dose acetyl-cholinesterase inhibitors with quaternary ammonium antimuscarinic drug (ACEI-QAAM), including but not limited to: ADAS (Alzheimer's disease assessment scale), MMSE, FAST, Neuropsychological Testing (Alzheimer's disease, Dementia with Lewy Bodies, Progressive Supranuclear Palsy, Multisystem Atrophy), UPDRS (Parkinson's Disease, Dementia with Lewy Bodies, Multisystem Atrophy) and appropriate scales of autistic symptoms and signs. Trials will need to be done for periods of time consistent with the tempo of the disease course, shorter for Dementia with Lewy Bodies, longer for Autism Spectrum Disorders.

Patients treated with acetyl-cholinesterase inhibitors in combination with quaternary ammonium anti-cholinergic muscarinic agents (ACEI-QAAM) (or other substances designed to improve CSF perfusion of the brain) can be studied for cognitive, affective, and functional improvement over time. In one preferred embodiment, the acetyl-cholinesterase inhibitor is rivastigmine and the quaternary ammonium anti-cholinergic muscarinic receptor antagonist is glycopyrrolate. Emerging side effects are unlikely due to the fact that medications involved in ACEI-QAAM have been available and studied for several decades in the United States and other developed countries.

For those patients presently exhibiting symptoms of acute delirium, in whom acetyl-cholinesterase inhibitor therapy is being administered, the prior art doses are commonly donepezil: 5-23 mg/day, galantamine: 4-24 mg/day, rivastigmine: 1.5 to 12 mg/day, physostigmine: 0.5 to 2 mg/day intravenous bolus or up to 10 mcg/minute intravenous infusion. Neostigmine and pyridostigmine have also been used, but dosing is not well defined.

In preferred embodiments of the methods described herein, the dosing for glycopyrrolate is about 0.5 to 4 mg twice a day, with a dosage of about 1-2 mg twice a day most preferred. Trospium is preferably administered at a rate of 20 mg twice a day or 60 mg of an extended release formulation once daily. Donepezil hydrochloride is administered at a rate of about 2 to 23 mg once a day, with a dosage range of about 5 to 10 mg once a day most preferred. Rivastigmine is dosed at 1.5 to 24 mg twice orally each day and galantamine at 4 to 12 mg twice a day.

In patients with cognitive disorders or other neurodegenerative diseases being treated with ACEI-QAAM, higher doses of all the acetylcholinesterase inhibitors are tolerated at at least four times the usual monotherapy dose. For rivastigmine, the maximum monotherapy dose in the US is currently 12 mg/day orally or 9.5 mg/day transdermally (the FDA recently approved the use of 13.5 mg/day transdermally, but the maximum orally approved dose is still 12 mg/day). In preferred embodiments, dosages up to 48 mg/day orally or 54 mg/day transdermally are preferably used. In one preferred embodiment, the daily dosage of the combination therapy is rivastigmine at 24 mg/day (or 19 mg transdermally) in combination with 2 mg of glycopyrrolate twice daily by mouth.

In one preferred embodiment, for patients presently exhibiting symptoms of dementia with Lewy bodies, a combination of rivastigmine and glycopyrrolate are administered to the patient. In one preferred embodiment, a minimum of 12 mg to 24 mg/day of rivastigmine is administered, either orally or transdermally. In a further preferred embodiment, a minimum of 19 mg to 24 mg/day of rivastigmine is administered. In another preferred embodiment, a minimum of 24 mg/day of rivastigmine is administered. In preferred embodiments, dosages up to 48 mg/day orally or 54 mg/day transdermally of rivastigmine are used. In one preferred embodiment, glycopyrrolate can be administered at the rate of 0.1 to 0.8 mg/day parenterally, or, orally, at the rate of 1 to 8 mg/day. In a further preferred embodiment, 1-2 mg of glycopyrrolate is administered, orally, twice a day.

For those patients being administered therapy for other cognitive disorders, including but not limited to, mild cognitive impairment, Alzheimer's disease, Parkinson's disease, Multisystem Atrophy, Dementia with Lewy Bodies, Frontotemporal Dementia, Progressive Supranuclear Palsy, Vascular Dementia, as well as those with biomarker and radiographic defined risks of developing such diseases, and Autism Spectrum Disorder, in one preferred embodiment, rivastigmine and glycopyrrolate are administered to the patient. In one preferred embodiment, a minimum of 12 mg to 24 mg/day of rivastigmine is administered, either orally or transdermally. In a further preferred embodiment, a minimum of 19 mg to 24 mg/day of rivastigmine is administered. In a further preferred embodiment, a minimum of 24 mg/day of rivastigmine is administered. In preferred embodiments, dosages up to 48 mg/day orally or 54 mg/day transdermally of rivastigmine are used. In one preferred embodiment, glycopyrrolate can be administered at the rate of 0.1 to 0.8 mg/day parenterally or, orally, at the rate of 1 to 8 mg/day. In a further preferred embodiment, 1-2 mg of glycopyrrolate is administered, orally, twice a day.

Data available with patients who have been treated with acetyl-cholinesterase inhibitors in combination with quaternary ammonium anti-cholinergic muscarinic agents for Dementia with Lewy Bodies (DLB) provide evidence of a disease modifying effect of this combination therapy.

The element of an acceptable reliable means of disease modification for neurodegenerative processes and Autism Spectrum Disorders based upon clearance of disadvantageous endogenous molecules by enhancing the CSF clearing mechanism through pharmacological means can be combined with mechanisms for screening and early diagnosis of such disorders. The resultant decline in the burden of neurodegenerative and undefinable developmental disorders will have significant economic potential for a sponsor, as well as significant social, medical, and economic benefits for society.

Example

Rivastigmine with Glycopyrrolate in Patients with Dementia with Lewy Bodies

Data available with patients who have been treated with acetyl-cholinesterase inhibitors in combination with quaternary ammonium anti-cholinergic muscarinic agents for Dementia with Lewy Bodies (DLB) provide evidence of a disease modifying effect. Dementia with Lewy Bodies is a progressive dementing disease with some features of Parkinsonism. It progresses faster than Alzheimer's Disease and provides an opportunity to observe a change in the deterioration of cognitive ability over time (Olichney J M et al. "Cognitive Decline is Faster in Lewy Body Variant than in Alzheimer's Disease". Neurology 1998; 51 (2)351, herein incorporated by reference).

Three patients were treated with the maximally tolerated dose of an acetyl-cholinesterase inhibitor, in this case, rivastigmine, in combination with 1-2 mg of glycopyrrolate administered orally twice daily to avoid side effects. This resulted in doses that were at least twice the maximum FDA approved top dose of oral or transdermal rivastigmine. The Mini-Mental State Examination, a standardized, rapid cognitive assessment that is widely used in clinical practice, was used to test the patients' cognitive ability over time.

Patient 1:

K M was a 65 year old woman with new onset of dementia with Lewy Bodies when she began treatment. She was treated with 24 mg/day of oral rivastigmine in combination with 1 mg of glycopyrrolate orally twice a day.

FIG. 1 compares the expected (100) results of the MMSE test for a patient with new onset of dementia with Lewy Bodies with the actual (150) MMSE test results for patient K M. The x-axis shows the number of months of treatment. When patient K M began treatment, her MMSE score was 16, below the expected score for MMSE at the onset of dementia with Lewy bodies. During the third month after treatment, K M's MMSE score increased to 30 (the highest score for the MMSE), and continued to be between approximately 28 and 30 for the remainder of the 36 month period shown in the figure. In comparison, the expected MMSE score at approximately 21 months is 15, and at the 35 month mark is less than 10. This is a remarkable improvement in cognitive function, and indicates that the combination treatment has dramatically slowed the progression of the disease. At the time of initiation of therapy, the patient was planning to be placed in a skilled nursing facility (a nursing home), but she currently resides in the community with her husband without additional assistance.

Patient 2:

A L was a 65 year old man with one year of symptoms of dementia with Lewy Bodies prior to the combination treatment. A L was treated with 19 mg/day of rivastigmine transdermally once daily in combination with 2 mg glycopyrrolate two times a day.

Figure 2:
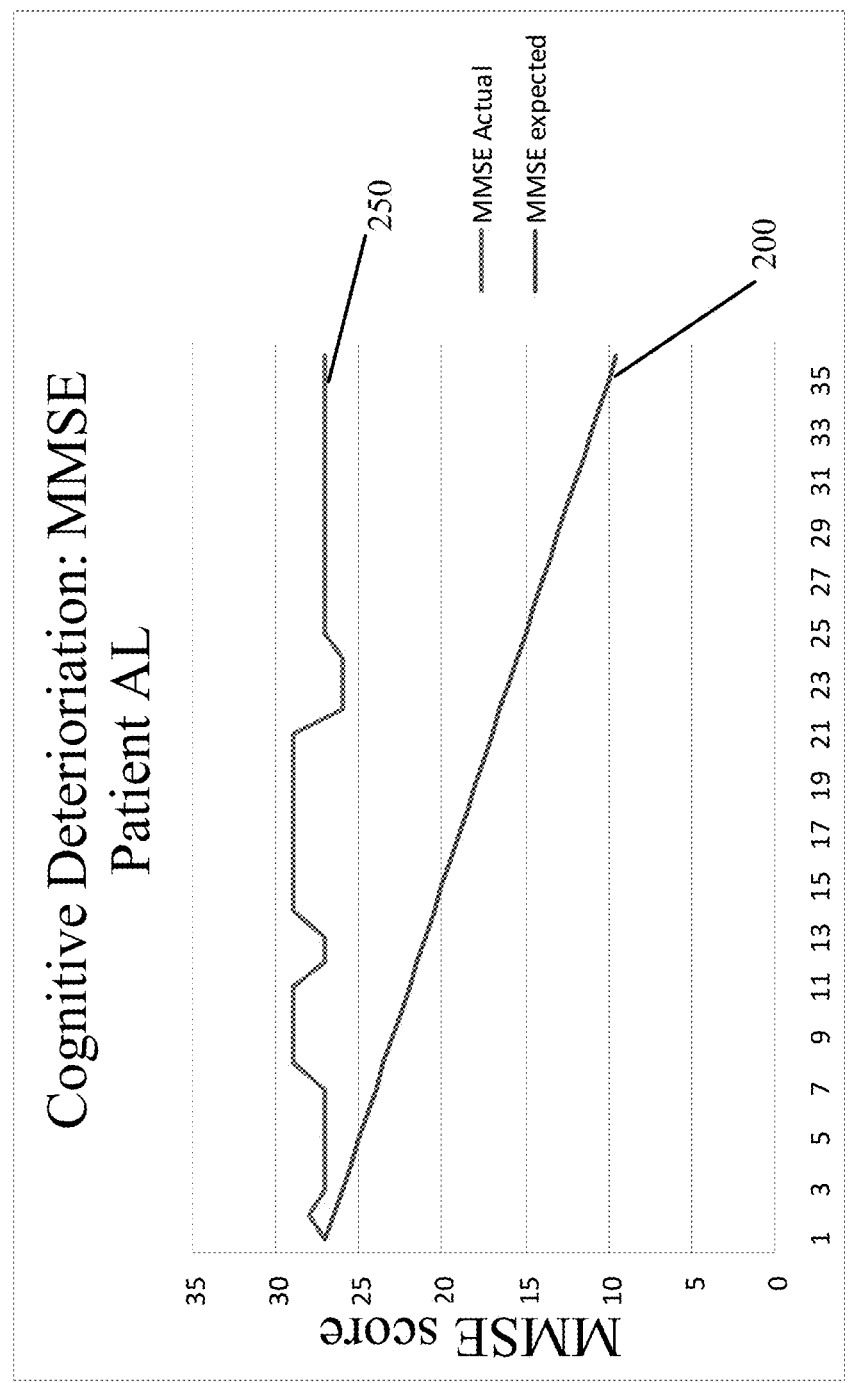
FIG. 2 shows

FIG. 2 compares the expected (200) results of the MMSE test based on A L's MMSE score at the beginning of his treatment for dementia with Lewy Bodies with the actual (250) MMSE test results for patient A L. The x-axis shows the number of months of treatment. When patient A L began treatment, his MMSE score was 27. A L's score remained between 26 and 30 during the 36 month period shown in the figure. In comparison, the expected MMSE score at approximately 21 months is 15, and at the 35 month mark is less than 10. This is a remarkable improvement in cognitive function, and indicates that the combination treatment has dramatically slowed the progression of the disease. This patient was expected to need nursing home care, and was being considered for hospice care at one point. He resides in the community with his wife, and vacations in Florida during the winter.

Patient 3:

R F was a 57 year old man when treatment was initiated. At the time treatment was initiated, R F had been showing symptoms of dementia with Lewy Bodies for two years.

Figure 3:
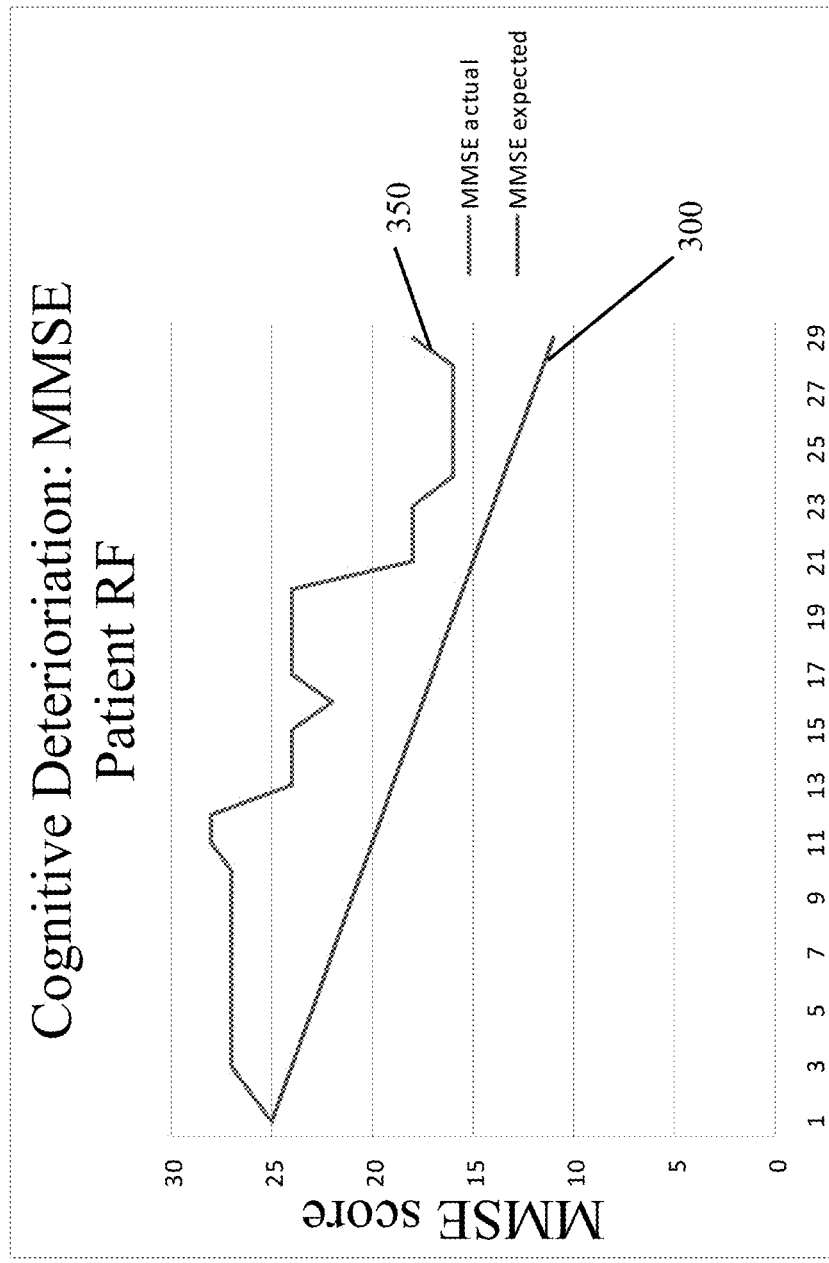
FIG. 3 shows disease progression in a patient, R F, versus expected disease progression.

FIG. 3 shows that R F's actual (350) MMSE scores over a 29 month period consistently exceeded the expected (300) MMSE scores. R F experienced clinical improvement when the treatment was initiated. For example, at 11 months, the expected MMSE score is approximately 20, and R F's score was approximately 28. Between 20 and 28 months, R F's scores fluctuated between 16 and 18, while the expected progression would be a decrease in the MMSE score from 15 to 11 during that time period. While R F had a clinical response to the treatment, it is unclear whether there was a real change in the underlying disease process. One reason for this potential difference in outcome includes an earlier age of onset (which may indicate a different mechanism underlying the disease). In addition, R F had previously abused alcohol, and may have been exposed to organophosphonate insecticides during his employment at a lawn care company. Such chemicals are an epidemiological risk for Parkinson's disease, which is another Lewy Body disorder. Despite these additional obstacles, patient R F clearly had symptomatic improvement. Patients with a history similar to R F's history may need higher doses of acetylcholinesterase inhibitors to get disease modification.

The patients' MMSE scores in FIGS. 1-3 over two to three years are shown in the figures compared to the published rate of expected decline (Olichney J M et al. "Cognitive Decline is Faster in Lewy Body Variant than in Alzheimer's Disease". Neurology 1998; 51 (2)351). There is no treatment for Dementia with Lewy Bodies, and the rate of expected decline is based on no treatment.

In addition to the measured scores, all three patients (K M, A L, and R F) have remained in the community living at home with spouses. Institutionalization was recommended prior to treatment for K M and A L.

Rates of institutionalization have been reported to be higher for dementia with Lewy bodies than for Alzheimer's Disease. (Olichney J M et al. "Cognitive Decline is Faster in Lewy Body Variant than in Alzheimer's Disease". Neurology 1998; 51 (2)351). Survival after diagnosis of dementia with Lewy bodies is also reported to be shorter for patients with Dementia with Lewy Bodies compared to Alzheimer's Disease (Williams M M et al., "Survival and mortality differences between dementia with Lewy bodies vs Alzheimer disease". Neurology. 2006; 67(11):1935; Lopez O L et al., "Predictors of progression in patients with AD and Lewy bodies", Neurology. 2000; 54(9):1774, both incorporated herein by reference).

Dementia with Lewy Bodies progresses faster that Alzheimer's Disease, which is the most common form of neurodegenerative dementia. The constellation of symptoms in dementia with Lewy Bodies includes vivid hallucinations, falling, precipitous drops in blood pressure and rapid fluctuations. The patients are usually intolerant of drugs used for psychosis. They have variable moods with a predisposition to depression. They have varying degrees of symptoms similar to Parkinson's disease. This results in a higher rate of institutionalization than with other dementia. The affective, functional and cognitive stability over time, as measured by MMSE and the ability to remain in a community dwelling, in this devastating disease indicates that the treatment is modifying the course of the underlying disease, and not merely treating symptoms.

Alternative Formulations for Glycopyrrolate

Currently available quaternary ammonium anti-cholinergic muscarinic receptor antagonists compositions occur as a salt, with the quaternary ammonium cation and a non-organic anion.

In preferred embodiments of the present invention, a quaternary ammonium anti-cholinergic muscarinic receptor antagonist includes a salt comprising an organic lipophilic anion as an anionic component of the salt. In some preferred embodiments, the lipophilic anion of the quaternary ammonium anti-cholinergic muscarinic receptor antagonist preferably includes a fatty acid including at least eight carbon molecules. In some preferred embodiments, the quaternary ammonium anti-cholinergic muscarinic receptor antagonist is glycopyrrolate or trospium.

The quaternary ammonium antimuscarinic drugs (QAAM) are particularly useful because of their ability to antagonize endogenous acetylcholine during periods of excessive acetylcholine production, or prolonged acetylcholine affect from physiologic and pharmacologic reasons. These compounds share the property that they do not appreciably penetrate the central nervous system (CNS), and glycopyrrolate bromide and trospium chloride have been particularly useful in treating patients in need of a peripheral anticholinergic effect on antimuscarinic receptors.

The same biochemical property that is advantageous in preventing CNS distribution, also limits intestinal absorption, requiring the currently available formulations of these medications to be taken in the absence of food, and resulting in incomplete and variable bioavailability in patients.

Glycopyrrolate hydrobromide is a quaternary ammonium salt with the chemical name of 3[(cyclopentylhydroxyphenylacetyl)oxy]-1,1-dimethyl pyrrolidinium bromide, a molecular formula of $C_{19}H_{28}BrNO_3$ and a molecular weight of 398.33.

Trospium chloride is a quaternary ammonium salt with the chemical name of Spiro [8-azoniabicyclo[3.2.1]octane-8,r-pyrrolidinium], 3-[(hydroxydiphenylacetyl)oxy]-, chloride, (α, 3β, 5α). The molecular formula of trospium chloride is $C_{25}H_{30}ClNO_3$ and its molecular weight is 427.97.

Enhancing the oral bioavailability of glycopyrrolate, trospium, and other QAAMs allows for administration of the medication without regard to food, and possibly without regard to other medications. It would also decrease the inter-subject variability in effect of the medication and reduce the effect of changes in gastrointestinal motility on drug absorption, because the degree of variability between patients is directly proportional to the time it takes to absorb a medication.

A QAAM is produced with a lipophilic anion as the anionic component of a salt. Structure activity analysis (SAR) suggests that an optimum lipophilic anion would be a fatty acid of at least 8 carbon molecules, so that the hydrophobic tail of the molecules would provide enhanced lipid solubility to counteract the positive charge of the ionized cationic QAAM molecule. In some preferred embodiments, the appropriate salts come from a family of medium and long chain fatty acids including, but not limited to: arachnic acid, stearic acid, palmitic acid, oleic acid, erucic acid, linoleic acid, arachidonic acid, or myristic acid.

The salt of the QAAM (cation) and the fatty acid (anion) can be produced through a common organic chemistry reaction referred to as "ion swapping". In such a reaction, the QAAM compound as the current elemental salt (glycopyrrolate hydrobromide, trospium chloride) is placed in solution with the elemental salt of a 3 fatty acid such as linolenic acid. The solution is subjected to variations in temperature, pH and agitation to produce an insoluble salt but is precipitated and collected as the supernatant fluid is removed. The precipitated salt is harvested, qualitatively and quantitatively identified and then stoichiometrically administered to animals. Quantitative serum and/or urine assays are used to make comparisons with the elemental salt of the QAAM, both in the presence and absence of food. Intravenous administration of the QAAM (example: glycopyrrolate) with quantitative serum and/or urine assay can be used as a reference standard for 100% bioavailability, and both the native compound and the synthesized salt are compared against this to establish their relative bioavailability in the presence and absence of food and other commonly co-administered medications.

In addition to the bioavailability studies mentioned above, quality studies would need to be done during the process to make sure there is no hydrolysis of the QAAM molecule in the process.

The synthesized fatty acids/QAAM salt are useful as an individual product for the treatment of various diseases involving excessive acetylcholine activity in humans and animals, whether these are produced by a pathologic process or the use of a medication (including but not limited to: overactive bladder, sialorrhea, diarrhea, bradycardia, hyperhidrosis, overactive gastric secretion, dumping syndrome, bronchospasm, vasomotor rhinitis). Enhanced bioavailability QAAM should be able to improve symptoms without causing significant central nervous system anti-cholinergic toxicity. Enhanced bioavailability allows for administration without regard to food, and may also allow for transdermal absorption to be enhanced to the level that transdermal formulations of this product would be practical. This could also be used in combination with acetylcholinesterase inhibiting drugs, or any other drug that increases acetylcholine tone.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. In a human patient suffering from a neurodegenerative cognitive disorder caused or facilitated by a decline of neurotransmitter chemical acetylcholine in a brain of the human patient, the neurodegenerative cognitive disorder selected from a group consisting of cognitive impairment and acute dementia, a method for improving cognitive function comprising administering to the patient a therapeutic amount of a combination of rivastigmine and glycopyrrolate, the glycopyrrolate having a oil/water partitioning coefficient of less than 1.0 at a physiological pH of 7.4.

2. The method of claim 1, comprising administering from about 1.5 to about 24 mg/day orally, or about 4.6 to about 17.4 mg/day by transdermal patch of rivastigmine.

3. The method of claim 1, comprising administering from about 0.1 to about 0.8 mg/day parenterally, or about 3.0 to about 8.0 mg/day orally of glycopyrrolate.

4. The method of claim 1, comprising administering the combination of from about 1.5 to about 24 mg/day, orally, or about 4.6 to about 17.4 mg/day transdermally of rivastigmine and from about 0.1 to about 0.8 mg/day, parenterally, or about 3 to about 8 mg/day, orally, of glycopyrrolate.

5. The method of claim 1, wherein the neurodegenerative cognitive disorder is selected from the group consisting of Alzheimer's Disease, Dementia with Lewy Bodies, Parkinson's Disease, Fronto-temporal dementia, and Progressive Supranuclear Palsy.

6. A method for treating a neurodegenerative cognitive disorder caused or facilitated by a decline of neurotransmitter chemical acetylcholine in a brain of a patient, the method comprising administering to the patient a therapeutic amount of glycopyrrolate and a therapeutic amount of rivastigmine, the glycopyrrolate having an oil/water partitioning coefficient of less than 1.0 at a physiological pH of 7.4.

7. The method of claim 6, wherein the neurodegenerative cognitive disorder is selected from the group consisting of Alzheimer's Disease, Dementia with Lewy Bodies, Parkinson's Disease, Fronto-temporal dementia, and Progressive Supranuclear Palsy.

8. The method of claim 6, comprising administering from about 1.5 to about 24 mg/day orally, or about 4.6 to about 17.4 mg/day by transdermal patch of rivastigmine.

9. The method of claim 6, comprising administering from about 0.1 to about 0.8 mg/day parenterally, or about 3.0 to about 8.0 mg/day orally of glycopyrrolate.

10. The method of claim 6, comprising administering the combination of from about 1.5 to about 24 mg/day, orally, or about 4.6 to about 17.4 mg/day transdermally of rivastigmine and from about 0.1 to about 0.8 mg/day, parenterally, or about 3 to about 8 mg/day, orally, of glycopyrrolate.

11. A method for treating Dementia with Lewy Bodies caused or facilitated by a decline of neurotransmitter chemical acetylcholine in a brain of a patient, the method comprising administering to the patient a therapeutic amount of glycopyrrolate and from about 1.5 to about 24 mg/day orally, or about 4.6 to about 17.4 mg/day by transdermal patch of rivastigmine, the glycopyrrolate having an oil/water partitioning coefficient of less than 1.0 at a physiological pH of 7.4.

12. The method of claim 11, comprising administering from about 0.1 to about 0.8 mg/day parenterally, or about 3.0 to about 8.0 mg/day orally of glycopyrrolate.

13. In a human patient suffering from a neurodegenerative cognitive disorder caused or facilitated by a decline of neurotransmitter chemical acetylcholine in a brain of the human patient, a method for improving cognitive function comprising administering to the human patient a therapeutic amount of a combination of an acetylcholinesterase inhibitor and a quaternary ammonium anti-cholinergic muscarinic receptor antagonist, the quaternary ammonium anti-cholinergic muscarinic receptor antagonist having an oil/water partitioning coefficient of less than 1.0 at a physiological pH of 7.4.

14. The method of claim 13, wherein the acetylcholinesterase inhibitor is donepezil.

15. The method of claim 13, wherein the quaternary ammonium anti-cholinergic muscarinic receptor antagonist is solifenacin.

16. The method of claim 13, wherein the acetylcholinesterase inhibitor is donepezil and the quaternary ammonium anti-cholinergic muscarinic receptor antagonist is solifenacin.

17. The method of claim 13, wherein the neurodegenerative cognitive disorder is selected from the group consisting of Alzheimer's Disease, Dementia with Lewy Bodies, Parkinson's Disease, Fronto-temporal dementia, and Progressive Supranuclear Palsy.

18. A method for treating a neurodegenerative cognitive disorder caused or facilitated by a decline of neurotransmitter chemical acetylcholine in a brain of a patient, the method comprising administering to the patient a therapeutic amount of an acetylcholinesterase inhibitor and a quaternary ammonium anti-cholinergic muscarinic receptor antagonist, the quaternary ammonium anti-cholinergic muscarinic receptor antagonist having an oil/water partitioning coefficient of less than 1.0 at a physiological pH of 7.4.

19. The method of claim 18, wherein the neurodegenerative cognitive disorder is selected from the group consisting of Alzheimer's Disease, Dementia with Lewy Bodies, Parkinson's Disease, Fronto-temporal dementia, and Progressive Supranuclear Palsy.

20. The method of claim 18, wherein the acetylcholinesterase inhibitor is donepezil.

21. The method of claim 18, wherein the quaternary ammonium anti-cholinergic muscarinic receptor antagonist is solifenacin.

22. The method of claim 18, wherein the acetylcholinesterase inhibitor is donepezil and the quaternary ammonium anti-cholinergic muscarinic receptor antagonist is solifenacin.

23. A method to inhibit undesired side effects of acetyl cholinesterase inhibitors used to treat a patient suffering from a cognitive disorder caused or facilitated by a decline of neurotransmitter chemical acetylcholine in a brain of the patient, the cognitive disorder selected from the group consisting of acute delirium and cognitive impairment, the method comprising administering to the patient a therapeutic amount of solifenacin, the solifenacin having an oil/water partitioning coefficient of less than 1.0 at a physiological pH of 7.4.

24. The method of claim 23, wherein the acetylcholinesterase inhibitor is donepezil.

25. In a human patient suffering from a neurodegenerative cognitive disorder caused or facilitated by a decline of neurotransmitter chemical acetylcholine in a brain of the human patient, the cognitive disorder selected from the group consisting of cognitive impairment and acute dementia, a method for improving cognitive function comprising administering to the patient a therapeutic amount of a combination of donepezil and glycopyrrolate, the glycopyrrolate having an oil/water partitioning coefficient of less than 1.0 at a physiological pH of 7.4.

26. The method of claim 25, comprising administering from about 2 to 20 mg donepezil.

27. The method of claim 25, comprising administering from about 0.1 to about 0.8 mg/day parenterally, or about 3.0 to about 8.0 mg/day orally of glycopyrrolate.

28. The method of claim 25, wherein the neurodegenerative cognitive disorder is selected from the group consisting of Alzheimer's Disease, Dementia with Lewy Bodies, Parkinson's Disease, Fronto-temporal dementia, and Progressive Supranuclear Palsy.

29. A method for treating a neurodegenerative cognitive disorder caused or facilitated by a decline of neurotransmitter chemical acetylcholine in a brain of a patient, the method comprising administering to the patient a therapeutic amount of glycopyrrolate and a therapeutic amount of donepezil, the glycopyrrolate having an oil/water partitioning coefficient of less than 1.0 at a physiological pH of 7.4.

30. The method of claim 29, wherein the neurodegenerative cognitive disorder is selected from the group consisting of Alzheimer's Disease, Dementia with Lewy Bodies, Parkinson's Disease, Fronto-temporal dementia, and Progressive Supranuclear Palsy.

31. The method of claim 29, comprising administering from about 0.1 to about 0.8 mg/day parenterally, or about 3.0 to about 8.0 mg/day orally of glycopyrrolate.

32. The method of claim 29, comprising administering from about 2 to 20 mg donepezil.

33. The method of claim 29, wherein the neurodegenerative cognitive disorder is Dementia with Lewy Bodies.

34. A method to inhibit undesired side effects of donepezil used to treat a patient suffering from a neurodegenerative cognitive disorder caused or facilitated by a decline of neurotransmitter chemical acetylcholine in a brain of the patient, the neurodegenerative cognitive disorder selected from the group consisting of acute delirium and cognitive impairment, the method comprising administering a therapeutic amount of glycopyrrolate, the glycopyrrolate having an oil/water partitioning coefficient of less than 1.0 at a physiological pH of 7.4.

35. The method of claim 34, comprising administering from about 0.1 to about 0.8 mg/day parenterally, or about 3.0 to about 8.0 mg/day orally of glycopyrrolate.

36. The method of claim 34, comprising administering from about 2 to 20 mg donepezil.

37. The method of claim 14, comprising administering from about 2 to 20 mg donepezil.

38. The method of claim 20, comprising administering from about 2 to 20 mg donepezil.

39. The method of claim 24, comprising administering from about 2 to 20 mg donepezil.

* * * * *